US010930392B2

(12) United States Patent
Pemberton et al.

(10) Patent No.: US 10,930,392 B2
(45) Date of Patent: Feb. 23, 2021

(54) SYSTEM AND METHOD FOR PROCESSING ECG RECORDINGS FROM MULTIPLE PATIENTS FOR CLINICIAN OVERREADING

(71) Applicant: General Electric Company, Schenectady, NY (US)

(72) Inventors: Matthew Lane Pemberton, Hubertus, WI (US); Brian J. Young, Slinger, WI (US)

(73) Assignee: General Electric Company, Schenectady, NY (US)

( * ) Notice: Subject to any disclaimer, the term of this patent is extended or adjusted under 35 U.S.C. 154(b) by 311 days.

(21) Appl. No.: 15/899,141

(22) Filed: Feb. 19, 2018

(65) Prior Publication Data

US 2019/0259496 A1 Aug. 22, 2019

(51) Int. Cl.
*G16H 40/20* (2018.01)
*A61B 5/0402* (2006.01)
*G16H 10/60* (2018.01)

(52) U.S. Cl.
CPC ........... *G16H 40/20* (2018.01); *A61B 5/0402* (2013.01); *G16H 10/60* (2018.01)

(58) Field of Classification Search
CPC ........ G16H 40/20; G16H 10/60; G16H 30/40; A61B 5/0402
See application file for complete search history.

(56) References Cited

U.S. PATENT DOCUMENTS

| 6,304,772 | B1 | 10/2001 | Taha et al. |
| 6,304,773 | B1 | 10/2001 | Taylor et al. |
| 6,490,479 | B2 | 12/2002 | Bock |
| 6,507,753 | B1 | 1/2003 | Xue et al. |

(Continued)

FOREIGN PATENT DOCUMENTS

| CN | 104382590 | 3/2015 |
| CN | 104473629 | 4/2015 |

(Continued)

OTHER PUBLICATIONS

PCT/US2019/018278 International Search Report/Written Opinion dated Jun. 14, 2019; 14 pages.

(Continued)

*Primary Examiner* — Amanda K Hulbert
*Assistant Examiner* — Natasha Patel
(74) *Attorney, Agent, or Firm* — Andrus Intellectual Property Law, LLP

(57) ABSTRACT

A method for processing ECG records from multiple patients for clinician overreading includes identifying an unread group of current ECG records from multiple patients awaiting clinician overreading. Each ECG record in the ungroup includes at least a current ECG data, a current waveform measurement, a current interpretative statement, and a serial comparison statement. A set of prioritization rules is applied with a processor to prioritize the current ECG records in the unread group into a prioritized order for clinician overreading based on at least one of the current waveform measurements, the current interpretive statements, and the serial comparison statements. The current ECG records are then presented in the prioritized order for clinician overreading.

19 Claims, 4 Drawing Sheets

(56) References Cited

U.S. PATENT DOCUMENTS

| | | |
|---|---|---|
| 6,687,685 B1 | 2/2004 | Sadeghi et al. |
| 7,469,287 B1 | 12/2008 | Castillo et al. |
| 7,702,382 B2 | 4/2010 | Xue et al. |
| 7,792,573 B2 | 9/2010 | McDougall et al. |
| 8,352,018 B2 | 1/2013 | Xue et al. |
| 9,078,572 B2 | 7/2015 | Brodnick |
| 9,131,843 B2 | 9/2015 | Myr |
| 9,254,092 B2 | 2/2016 | Albert et al. |
| 9,351,652 B2 | 5/2016 | Dziubinski et al. |
| 2003/0073914 A1 | 4/2003 | Taha |
| 2006/0079795 A1 | 4/2006 | Busche |
| 2006/0217623 A1 | 9/2006 | Morganroth |
| 2007/0027630 A1 | 2/2007 | Sanchez |
| 2007/0239490 A1* | 10/2007 | Sullivan ............... G06Q 30/02 705/3 |
| 2009/0131759 A1* | 5/2009 | Sims .................... A61B 5/1135 600/301 |
| 2013/0085405 A1 | 4/2013 | Bera |
| 2013/0261403 A1 | 10/2013 | Young |
| 2016/0135700 A1 | 5/2016 | Gregg |
| 2016/0183833 A1 | 6/2016 | Kuppuraj |
| 2017/0105683 A1 | 4/2017 | Xue |

FOREIGN PATENT DOCUMENTS

| | | |
|---|---|---|
| CN | 104783782 | 7/2015 |
| EP | 1179319 | 2/2002 |
| JP | 4841028 | 4/2001 |

OTHER PUBLICATIONS

GE Healthcare, "GE EK-Pro Arrhythmia Algorithm", D000783131, 2010 General Electric Company.

Xue, J., unpublished U.S. Appl. No. 15/806,009, filed Dec. 6, 2017.

* cited by examiner

SYSTEM AND METHOD FOR PROCESSING ECG RECORDINGS FROM MULTIPLE PATIENTS FOR CLINICIAN OVERREADING

BACKGROUND

Electrocardiograph (ECG) monitoring is a frontline tool for patient evaluation, and thus healthcare facilities manage a high volume of patient ECG recordings. Various software systems are available for automatically reviewing and assessing ECG data, such as to provide waveform measurements of various aspects of the ECG waveform, as well as to provide interpretive statements of the ECG data. For example, current software systems contain algorithms that automatically detect and report the presence of certain rhythm abnormalities or indices of heart disease or heart attack. Programs and systems are also available to compare ECG recordings taken over time so as to track and assess a change in a patient's ECG recording between a previous ECG recording taken at a previous date and a current ECG recording.

However, automated ECG processing is imperfect, and automated ECG assessments must be reviewed and confirmed or modified by a clinician. The review process is performed manually and is time consuming. In certain healthcare facilities and settings, such manual ECG review process by a clinician may take days to complete, depending on the backlog of unread ECGs and staff availability for overreading.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a method for processing ECG records from multiple patients for clinician overreading includes identifying an unread group of current ECG records from multiple patients awaiting clinician overreading. Each ECG record in the unread group includes at least a current ECG data, a current waveform measurement, a current interpretative statement, and a serial comparison statement. A set of prioritization rules is applied with a processor to prioritize the current ECG records in the unread group into a prioritized order for clinician overreading based on at least one of the current waveform measurements, the current interpretive statements, and the serial comparison statements. The current ECG records are then presented in the prioritized order for clinician overreading.

In one embodiment, a system for processing ECG records for multiple patients for clinician overreading includes a database containing an unread of current ECG records from multiple patients awaiting clinician overreading. Each current ECG record includes at least a current ECG data, a current waveform measurement, a current interpretive statement, and a serial comparison statement. A triage module is executable on the processor to apply a set of prioritization rules to prioritize the current ECG records in the unread group for clinician overreading based on at least on of the current waveform measurements, the current interpretive statements, and the serial comparison statements.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Healthcare facilities are often challenged with overreading and verifying the massive amounts of ECG records generated by patient monitoring systems in the healthcare facility. Thus, it sometimes takes one or two days before an ECG record is overread and confirmed by a clinician. In current systems, the unread ECG records are ordered according time, so that the clinician reviews the ECG recordings in chronological order according to the time that the record was made by the ECG monitor. This means that overreading of all ECG recordings is significantly delayed, including ECG recording containing abnormalities requiring urgent attention and medical care for the respective patient. The present inventors have recognized that such a delay is problematic where urgent matters that would be detected during the clinician overreading process are not detected as quickly as they could be or should be.

Upon recognition of the forgoing problems and challenges with ECG overreading, the inventors developed the disclosed system and method whereby ECG records awaiting clinician overreading are prioritized in order to expedite review of the ECG recordings that are most likely to be problematic and indicate a need for immediate clinical intervention for the patient. Thereby, clinician overreading resources are used more efficiently and patient care is improved.

Figure 1:
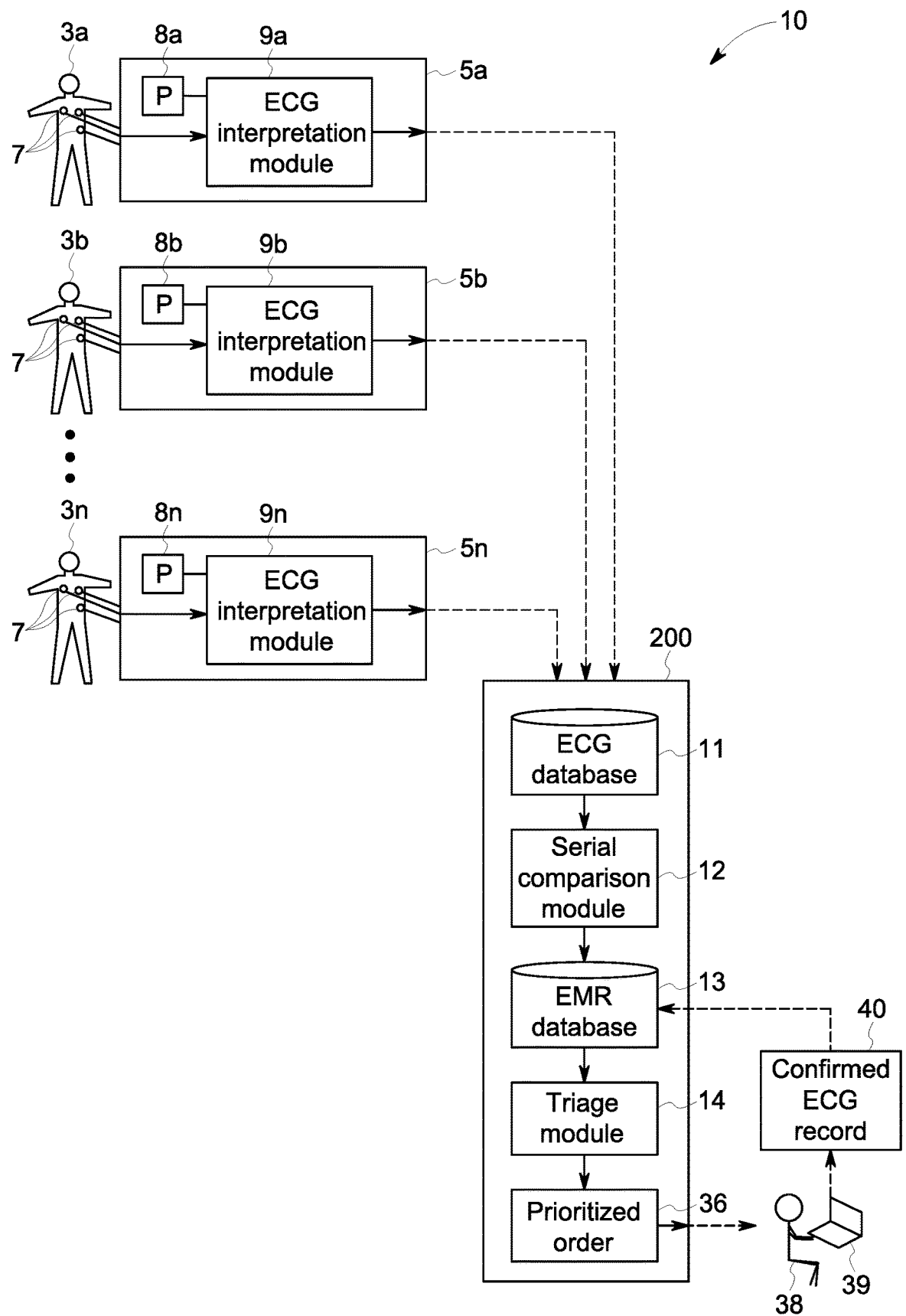
FIG. 1 schematically depicts one embodiment of a system for processing ECG recordings from multiple patients for clinician overreading.

FIG. 1 depicts one embodiment of a system 1 for processing current ECG records 22 awaiting clinician overreading. The current ECG records 22 originate from multiple different patients 3a, 3b-3n. In the Figure, multiple ECG monitors 5a-5n record time series of ECG data from patients 3a-3n. In a typical embodiment, each ECG monitor 5 receives potentials recorded via electrodes 7, such as 10 electrodes attached to the respective patient 3a-3n in order to generate a standard twelve lead ECG recording. However, in various embodiments the ECG monitor 5 may receive cardiac potentials from a different number of electrodes on the respective patient 3, such as to record a three lead or five lead ECG, or even a 15 lead ECG. The ECG monitor 5 generates ECG data recorded from each of the leads over a period of time, such as a ten second record of ECG data from each lead. Various other recording intervals are possible and known, such as intervals of thirty seconds, or even longer.

The ECG data recorded at the ECG monitor 5 is processed by an ECG interpretation module 9. In the depicted embodiment, each ECG monitor 5a, 5b-5n is equipped with its own ECG interpretation module 9a, 9b-9n to interpret the ECG data locally within the respective ECG monitor 5a, 5b-5n. The ECG interpretation module 9a, 9b-9n is a set of software instructions executable on the processor 8a, 8b-8n of the patient monitor 5a, 5b-5n in order to generate waveform measurements of the ECG data and/or to generate interpretive statements of the ECG data. One such system is the Marquette 12SL® ECG Analysis Program by General Electric Company of Schenectady, N.Y., which is a computerized analysis program providing measurements of heart rate, axis, intervals, and durations of the heartrate waveform, as well as interpretive statements offering automated ECG data analysis, such as arrhythmia detection, pace detection, QT interval issues, etc. In other embodiments, the ECG interpretation module 9 may be provided in the central computing system 200 or other centralized ECG processing system receiving ECG records from the various patient monitors 5a, 5b-5n in a healthcare facility or network. There, the ECG data recorded by each ECG monitor 5a, 5b-5n would be communicated to the central computing system 200 (or other centralized ECG processing system), where each ECG data set is processed by the ECG interpretation module 9. The output of the centralized ECG interpretation module 9, along with the ECG data recorded by the respective ECG monitor 5a, 5b-5c, would be recorded in the ECG database 11.

Figure 2:
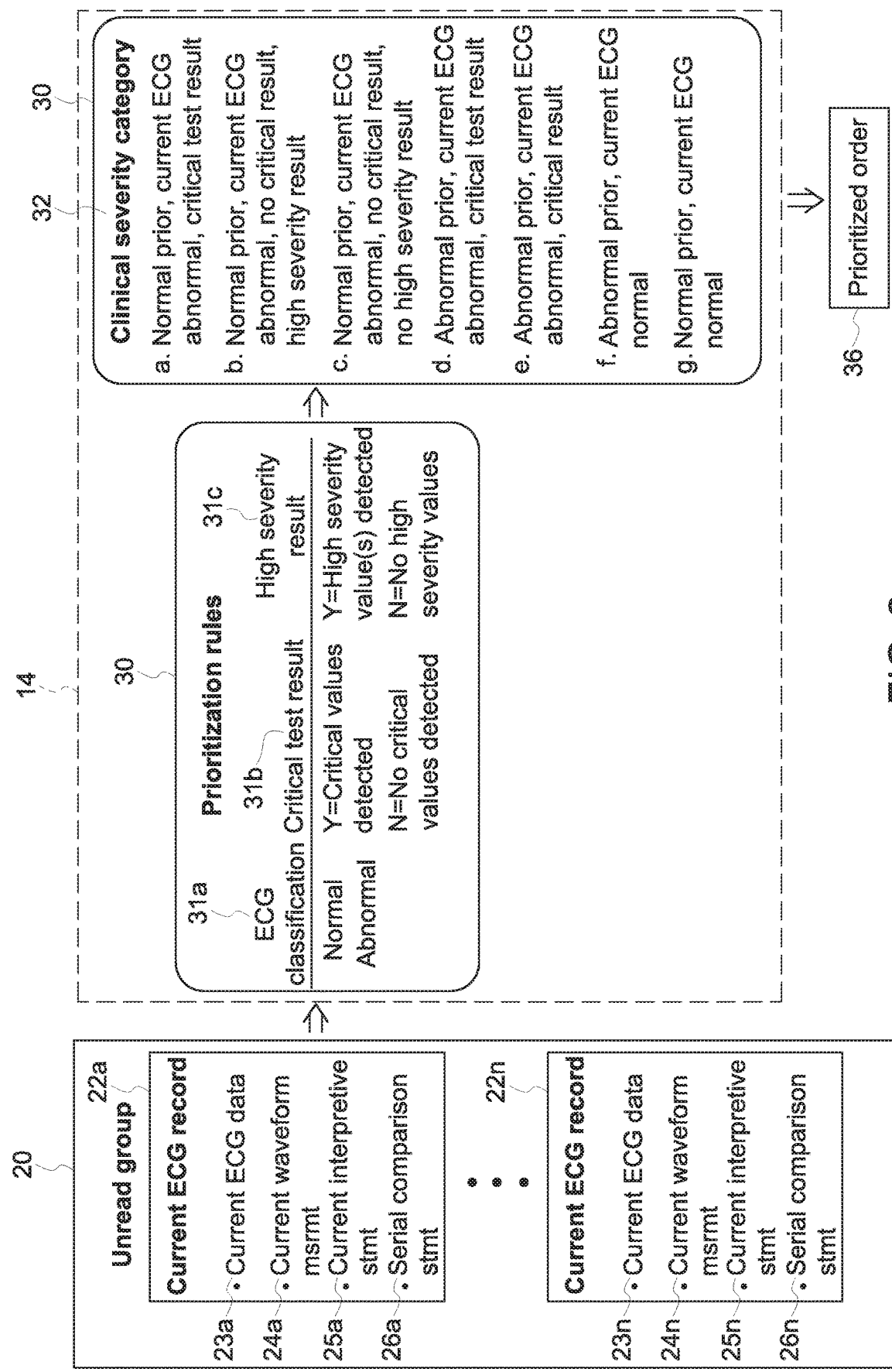
FIG. 2 schematically depicts one embodiment of a system and method for processing ECG recordings from multiple patients for clinician overreading.

The ECG database 11 stores the ECG record relating to each current ECG from each ECG monitor 5a, 5b-5n. With further reference to FIG. 2, each current ECG record 22 includes the current ECG data 23 recorded from the patient, one or more current waveform measurements 24 of the current ECG data, and one or more current interpretive statements 25 of the current ECG data, as well as any other information generated by the ECG interpretation module 9. The current ECG record 22 may further include one or more serial comparison statements 26 generated by a serial comparison module 12 based on a comparison between the current ECG record and a previous ECG record for the respective patient 3a, 3b-3n. For example, the serial comparison statement 26 notes any abnormalities in a current ECG data that were not present in a previous ECG data, as well as abnormalities in a previous ECG data that are no longer present in the current ECG data. Certain existing software products and systems compare two or more ECGs, such as a current ECG record and a most-recent previous ECG record for a particular patient, and provide clinical information on the differences between the two records. By way of example, the serial comparison module 12, the ECG interpretation module 9, and the ECG database 11 may comprise part of the MUSE Cardiology Information System provided by General Electric Company of Schenectady, N.Y.

The serial comparison module 12 and/or the ECG interpretation module 9 may be configured to detect critical values within the current ECG record 22. Critical values are values set according to a healthcare facility's critical values policy, which is a requirement by the Joint Commission on Accreditation of Healthcare Organization (JCAHO). For example, critical values may be detected at the ECG interpretation module 9a, 9-9n within each ECG monitor 5a, 5b-5n, which analyzes and compares the recorded ECG data against the critical values stored therein. In certain examples, a critical values event may generated at the patient monitor for alerting a clinician to the detection of a critical value, which may include alarming at the location of the patient monitor 5a, 5b-5n or at a nurses station or central monitoring station, or both. Alternatively or additionally, critical values may be detected by the serial comparison module 12, such as a serial comparison critical value indicating a critical change between a previous ECG record and a current ECG record.

In addition to being stored at the ECG database 11, the ECG record may also be stored in an electronic medical record (EMR) database 13. However, at that point the ECG record 22 has not been reviewed by a physician or other clinician capable of providing competent overreading, and thus comprises part of an unread group 20 of current ECG records 22a-22n awaiting clinician overreading. In order to facilitate efficient overreading to improve patient care, the inventors developed the disclosed system 10 comprising a triage module 14 that prioritizes the current ECG records 22a-22n in the unread group 20 for clinician overreading. Specifically, the triage module 14 includes software instructions applying a set of prioritization rules for prioritizing the current ECG records 22a-22n in the unread group 20 for clinician overreading based on at least one of the current waveform measurements 24a-24n, the current interpretative statements 25a-25n, and the serial comparison statements 26a-26n.

The triage module 14 may be configured to present the current ECG records 22a-22n in the unread group 20 in a prioritized order 36 for clinician overreading whereby ECG records that are most likely to represent time-sensitive patient issues will be prioritized so as to expedite their review ahead of ECG records that are less likely to represent time-sensitive health issues. For example, the current ECG records in the unread group may be categorized into one of at least two or more clinical severity categories based on at least the current interpretive statements and the serial comparison statements. Within each clinical severity category, the current ECG record may then be ordered from oldest to newest according to the test date and time at which the ECG data was collected from the patient 3a, 3b-3n by the patient monitor 5a, 5b-5n, thereby creating categorized ECG records. The triage module 14 then creates the prioritized order 36 for clinical overreading by ordering the categorized ECG records according to a pre-set ranking of the clinical severity category designations.

The current ECG records 22a-22n in the unread group 20 are then presented to the clinician in the prioritized order 36. Each ECG record 22 is then overread by a clinician 38 in to generate a confirmed ECG record 40, which may approve of or modify the automatically-generated information in the current ECG record 22, including the current waveform measurement(s) 24, current interpretive statement(s) 25, and/or serial comparison statement(s) 26. The confirmed ECG record 40 is then stored in the EMR database 13 to become part of the patient's medical record. The confirmed ECG record 40 may also be stored in the ECG database 11, such as for use in future comparisons of ECG data for the respective patient 3 by the serial comparison module 12.

FIG. 2 illustrates one example of prioritization rules and categorization by a triage module 14. An unread group 20 of current ECG records 22a-22n is provided to the triage module 14. For example, the current ECG records 22a-22n in the unread group 20 may initially be ordered chronologically, such as according to the test date and time and/or the order of receipt at the computing system 200, or may be provided in any order, including random order. Each current ECG record 22a-22n includes current ECG data 23a-23n, one or more current waveform measurements 24a-24n, one or more current interpretation statements 25a-25n, and one or more serial comparison statements 26a-26n. The unread group 20 is then prioritized by the triage module 14 and presented as a prioritized order 36 of current ECG records 22a-22n for clinician review.

Specifically, the triage module 14 executes instructions applying a set of prioritization rules 30 that categorize each of the current ECG records 23a-23n into one of at least two clinical severity categories (e.g., 32a-32g). In the depicted example, the prioritization rules 30 include classifying each current ECG data 23 into at least normal or abnormal ECG classifications 31a. In certain embodiments, the ECG classification 31a may further include one or more "borderline" designations, such as a borderline normal and/or a borderline abnormal, which may further be utilized to categorize the records into clinical severity categories 32. The prioritization rules 30 may further classify each current ECG record 22a-22n based on the ECG classification 31a of a previous ECG record. For example, information may be available in the serial comparison statement 26 or other aspect of the current ECG record 22 classifying the previous ECG data as normal or abnormal. Alternatively or additionally, the triage module 14 may make the normal/abnormal classification 31a determination for the previous ECG data, such as by accessing the previous ECG record or gleaning relevant information from the current ECG record 22.

The prioritization rules 30 may further include determining the presence or absence of a critical test result 31b, where a positive critical test result 31b indicates that critical values were detected, such by the ECG interpretation module 9 and/or the serial comparison module 12, and a negative critical test result 31b indicates that no critical values were detected. Thus, a positive critical test result 31b indicates that some critical value was detected, while the absence of a critical test result 31b indicates that none of the possible critical values were detected. As discussed above, the critical values, and thus the critical test result 31b, are identified according to a healthcare facility's critical values policy pursuant to JCAHO requirements.

Similarly, the prioritization rules 30 may include instructions identifying the presence or absence of a high severity result 31c, wherein the presence of a high severity result 31c indicates any one of a predefined list of values, measurements, or statements, such as a predefined list of arrhythmias or heart attack indicators. Thus, the positive critical test result 31c indicates that at least one of the predefined list of values was present, while the absence of a high severity result 31c indicates that none of the predefined list of indicators were present in the relevant current ECG record 22a-22n. High severity values may include, for example, current interpretive statements or serial comparison statements indicating the presence of ventricular tachycardia, bradycardia, acute myocardial infarction, acute coronary syndrome (ACS), hyperkalemia, atrial fibrillation (AFIB), and/or others. The list of high severity values that trigger a high severity result may be configurable at the system level, such as based on facility needs. The high severity result 31c enables prioritization rules 30 that capture certain values, such as rhythm abnormalities and/or indices of heart attack, which may not be critical values established by the healthcare facility's critical values policy. In an exemplary embodiment, each of the ECG classification 31a (which may be a separate classification for the prior ECG and the current ECG), the critical test result 31b, and the high severity result 31c can have one of two values, such as 1/0 or +/−. In other examples, each of the ECG classification 31a, the critical test result 31b, and the high severity result 31c can be any one of three or more values.

The prioritization rules 30 classify each current ECG record 22a-22n in the unread group 20 into a clinical severity category 32. Any number of two or more clinical severity categories 32 may be available, depending on the configuration of the prioritization rules 30, which provide a means for ranking each current ECG record 22a-22n and for establishing the prioritized order 36. In the depicted example, the prioritization rules 30 categorize each current ECG record 22a-22n into one of seven clinical severity categories 32a-32g. In the depicted example, the first clinical severity category includes those current ECG records 22a-22n having a normal prior ECG and an abnormal current ECG (based on the ECG classification 31a and/or based on the serial comparison statement 26), and where a critical test result 31b is present. Thus, where the current ECG record 22 represents a change from normal to abnormal and a critical test result is present, the current ECG record is placed in the first clinical severity category 32a. Depending on how the clinical severity categories are ordered to generate the prioritized order 36, those current ECG records 22a-22n categorized into the first clinical severity category 32a are able to be reviewed the soonest by the overreading clinician.

The ECG records in the first clinical severity category 32a are likely to represent an urgent situation for a patient. Moreover, it may be preferable to prioritize critical test results first because they represent the presence of a value listed in the facility's critical values policy upon which they are measured by JCAHO. However, other priority orders of the clinical severity categories 32a-32c are possible. For example, one or more additional clinical severity categories may be made based on the presence or absence of a high severity result 31c, which can further refine the prioritization process. In embodiments where the triage module 14 identifies high severity results 31c, newly abnormal ECG records with the presence of both a critical test result 31b and a high severity result 31c may be ranked first in the prioritized order 36. Alternatively, newly abnormal ECG records with the presence of a high severity result 31c may be ranked first in the prioritized order 36, above ECG records with a positive critical test result 31b but without a high severity result 31c. In the example at FIG. 2, a second clinical severity category 32b designates those current ECG records 22a-22n having a normal prior ECG and an abnormal current ECG, where no critical test result 31b is present but a high severity result 31c is present. In still other embodiments, the high severity result 31c may not be identified at all.

The third clinical severity category 32c exemplified at FIG. 2 designates current ECG records 22a-22n having a normal prior ECG record and an abnormal current ECG record, but where there is no critical test result and no high severity result. A forth clinical severity category 32d designates those current ECG records 22a-22n having an abnormal prior ECG and an abnormal current ECG, and where a critical test result is present. A fifth clinical severity category 32e is established for those current ECG records 22a-22n having an abnormal prior ECG and an abnormal current ECG where no critical test result is present. A sixth clinical severity category 32f designates those current ECG records 22a-22n having an abnormal prior ECG, but where the current ECG is normal. Finally, a seventh clinical severity category 32g designates those current ECG record 22a-22n having both a normal prior ECG and a normal current ECG.

Any number of other clinical severity categories 32 may be established within the triage module 14 to enable generation of the prioritized order 36. For example, additional categories could be established for continued abnormal ECG records based on the presence or absence of the high severity result, similar to the utilization of the high severity result for the first, second, and third clinical severity categories 32a-32c.

The prioritized order 36 is then established by ordering the current ECG records 22a-22n based on the clinical severity category 32a-32g designations. In certain embodiments, the triage module 14 may first organize the current ECG records 22a-22n within each clinical severity category 32a-32g, such as in chronological order based on the test date and time of the respective current ECG records 22a-22n in that category. Maintaining the chronological order of the records in each category, the prioritized order 36 is then established based on a ranking of the clinical severity categories 32a-32g. For example, the clinical severity categories 32a-32g may be ranked in the order presented in FIG. 2—i.e, with the current ECG records 22a in the first clinical severity category 32a prioritized first, the current ECG records 22a-22n in the second clinical severity category 32b presented second, and so on. However, the clinical severity categories 32a-32g may be ranked in any other order, which may be adjustable or configurable, such as by the administrator of the system 10 and/or by the overreading clinician. To provide just one example, the fourth clinical severity category 32d may be prioritized over the third clinical severity category 32c, thereby to prioritize the presence of a critical test result 31b over those records representing a shift from normal to abnormal but not having any critical value.

The prioritized order 36 of current ECG records 22a-22n are then presented to the overreading clinician 38, who reviews the ECG records in order to create the confirmed ECG record 40 for each of the current ECG records 22a-22n. The prioritized order 36 of current ECG records 22a-22n may be presented to the clinician via a user interface, such as at the local computing system 39 through which the clinician 38 is accessing the records. In various embodiments, the user interface of the local computing system 39 includes a digital display device and a user input means, such as a touch screen in conjunction with the digital display for receiving touch input from the user, and/or a mouse, keyboard, or other known user input device. For example, the local computing 39 may operate software comprising part of the triage module 14, or the local computing system 39 may operate a separate software module enabling clinician review that receives the prioritized order 36 from the computing system 200 and communicates the confirmed ECG records 40 back to the computing system 200 for storage in the EMR database 13 and/or the ECG database 11.

Figure 3:
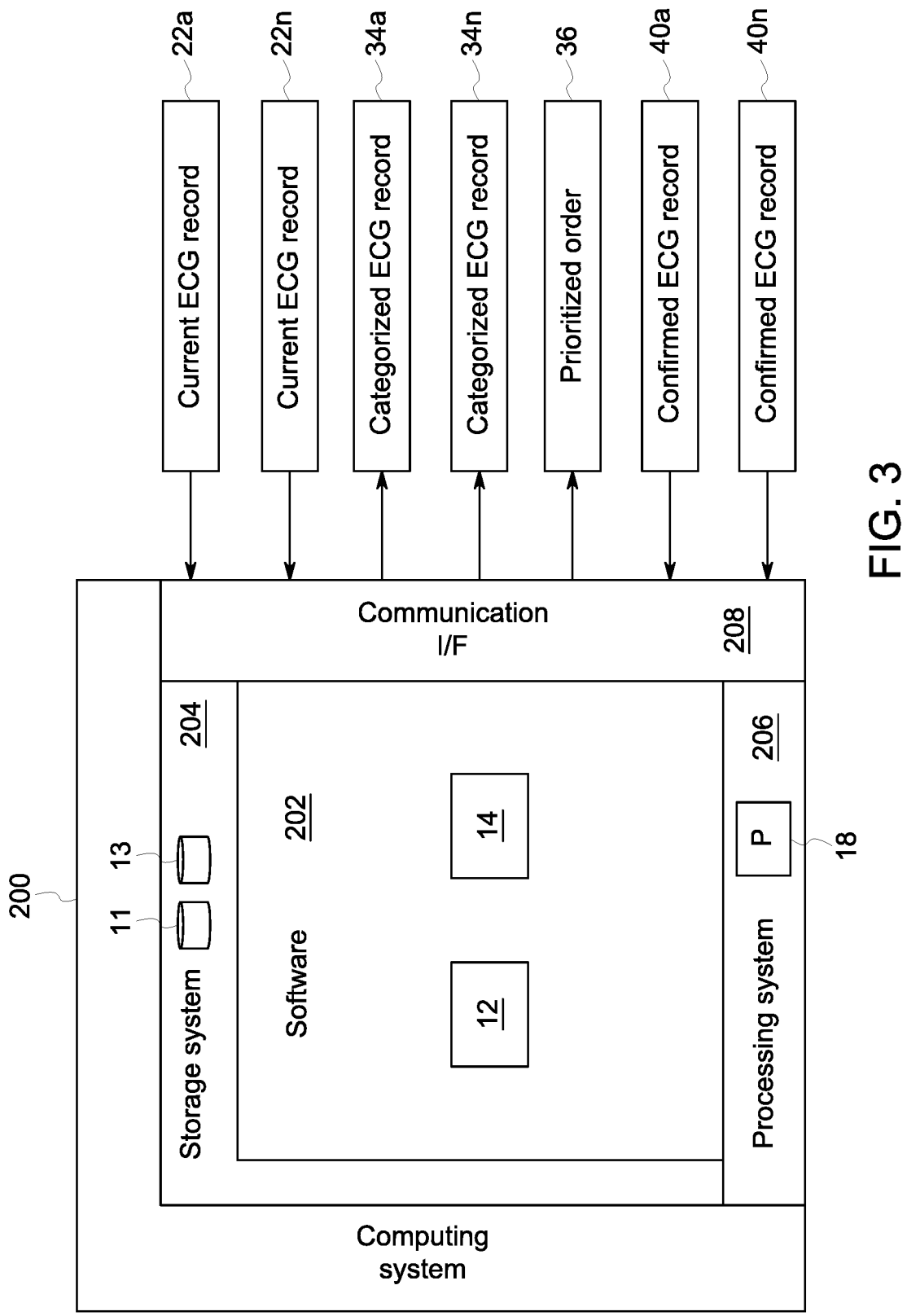
FIG. 3 is a schematic diagram of an exemplary computing system incorporated in one embodiment of a system for processing ECG recordings from multiple patients for clinician overreading.

FIG. 3 provides a schematic diagram of an exemplary computing system 200 that includes a processing system 206, storage system 204, software 202, and a communication interface 208. The processing system 206 loads and executes software 202 from the storage system 204, including the serial comparison module 12 and the triage module 14, which are applications within the software 202. Each of the modules 12 and 14 include computer-readable instructions that, when executed direct the processing system 206 to operate as described in herein in further detail. The triage module 14 receives the current ECG records 22a-22n and categorizes each record to generate categorized ECG records 34a-34n according to the steps described and exemplified above. In certain embodiments, the categorized ECG records 34a-34n may not be separately outputted or stored, and the categorization may simply be for internal usage within the triage module 14. The prioritized order 36 of current ECG records 22a-22n is outputted for clinician overreading, such as outputted to the local computing system 39 which facilitates presentation of the prioritized order 36, receipt of input from a clinician, and creation of the confirmed ECG record 40a-40n for each received current ECG record 22a-22n. The confirmed ECG records 40a-40n are then stored in the EMR database 13 and/or the ECG database 11.

Although the computing system 200 as depicted in FIG. 3 includes one software 202 encapsulating one serial comparison module 12 and one triage module 14, it should be understood that one or more software elements having one or more modules may provide the same operation attributed herein to the two separate modules 12 and 14. Likewise, the functionality described herein as comprising the ECG interpretation module 9 could also be incorporated within the aforementioned single software program and such implementations are considered to be within the scope of the description. Similarly, while description provided herein refers to a computing system 200 and a processing system 206, it is to be recognized that implementations of such systems can be performed using one or more processors 18, which may be communicatively connected, and such implementations are considered to be within the scope of the description.

The processing system 206 includes at least one processor 18, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the ECG database 11 and the EMR database 13, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device, but may also be implemented across multiple storage devices or sub-systems. For example, the software 202 may be stored on a separate storage device than the ECG database 11 and/or the EMR database 13. Likewise, each of the databases 11 and 13 may be stored on separate storage devices. Similarly, the ECG database 11 and/or the EMR database 13 may be stored, distributed, and/or implemented across one or more storage media or group of storage medias, and each database 11 and 13 may encompass multiple different sub-databases at different storage locations and/or containing different information which may be stored in different formats. By way of example, the ECG database 11 may comprise part of a MUSE ECG management system housing ECG records and other related data. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as with ECG monitors 5a-5n (or with a central ECG monitoring system that aggregates the ECG data from the individual monitors) and/or with the local computing system 39 utilized by the overreading clinician 38 to generate the confirmed ECG records 40a-40n.

Figure 4:
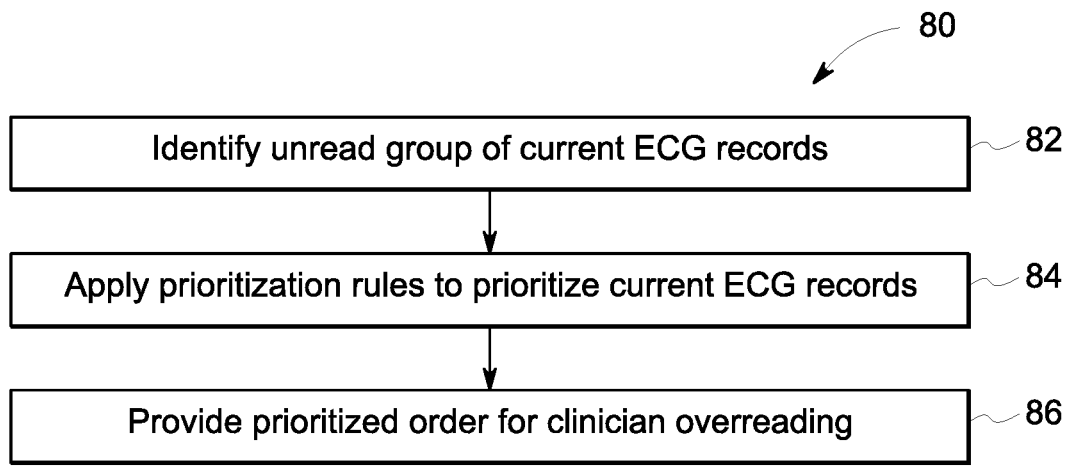
FIGS. 4 and 5 depict embodiments of methods, portions thereof, for processing ECG recordings from multiple patients for clinician overreading.
Figure 5:
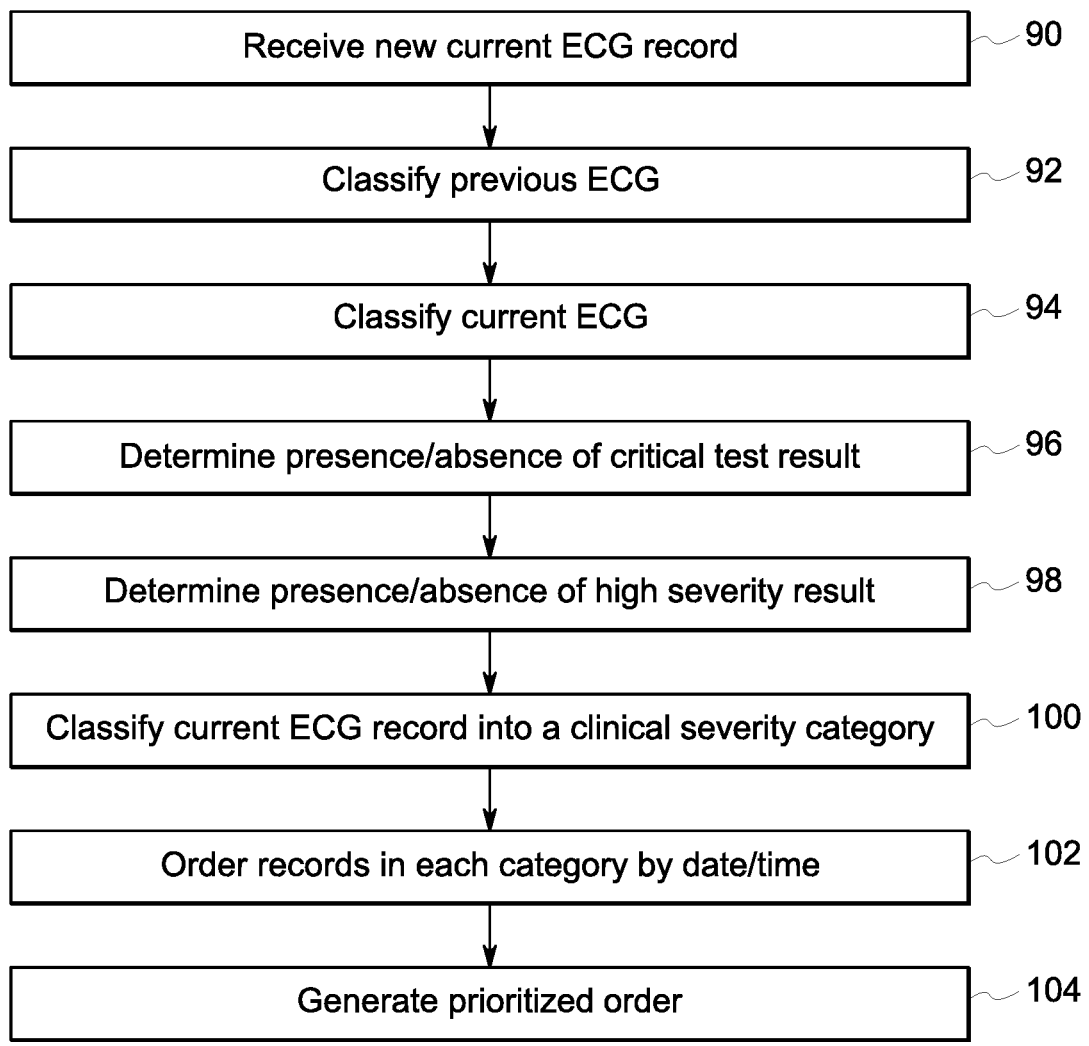

FIGS. 4 and 5 depict embodiments of a method 80, or portions thereof, for processing ECG records from multiple patients. An unread group 20 of current ECG records 22a-22n is identified at step 82. Prioritization rules are applied at step 84 to prioritize the current ECG records in the unread group for clinician overreading based on at least one of the current waveform measurements, the current interpretative statements, and the serial comparison statements. The prioritized order of current ECG records 22 is then provided at step 86 for clinician overreading.

FIG. 5 depicts one embodiment of a set of prioritization rules, such as steps that may be executed by the triage module 14 for prioritizing the current ECG records 22 in the unread group 20. Each unclassified current ECG record 22 is received at step 90 and the previous and current ECG records are given an ECG classification 31a at steps 92 and 94, such as classified as either normal or abnormal. The respective current ECG record 22 is reviewed at step 96 to determine the presence or absence of a critical test result 31b. For example, the critical test result may be deemed present where any one of the current ECG data 23, the current waveform measurement 24, the current interpretive statement 25, and/or the serial comparison statement 26 indicates a value identified as a critical value by the healthcare facility's critical values policy. Step 98 is executed to determine the presence or absence of a high severity result 31c which, as described above, indicates the presence of one or more high severity values. Similar to the critical test result 31b assessment, the high severity result 31c assessment involves assessing one or more of the current ECG data 23, the current waveform measurements 24, the current interpretive statements 25, and/or the serial comparison statements 26 of the respective ECG record 22 in order to detect the presence or absence of any value on the list of high severity values configured for the system 10. At step 100 the respective current ECG record 22 is then classified into one of at least two clinical severity categories 32, such as into one of the seven exemplary clinical severity categories 32a-32g illustrated and discussed above with respect to FIG. 2. The current ECG records 22 within each category are organized at step 102, such as by test date and time so that the records within each category are organized chronologically. The prioritized order 36 is then generated at step 104 based on a ranking of the clinical severity categories 32a-32g, and the current ECG records 22 are presented to the overreading clinician 38 in the prioritized order 36.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for processing ECG records from multiple patients for clinician overreading, the system comprising:
    a database containing an unread group of current ECG records from multiple patients awaiting clinician overreading, wherein each current ECG record in the unread group includes at least:
        a current ECG data recorded from a patient,
        a current waveform measurement of the current ECG data,
        a current interpretive statement of the current ECG data, and
        a serial comparison statement comparing at least one of the current waveform measurements to previous waveform measurements of a previous ECG data from the patient and the current interpretive statements to previous interpretive statements of the previous ECG data from the patient;
    a processor;
    a triage module executable on the processor to apply a set of prioritization rules to prioritize the current ECG records in the unread group for clinician overreading based on at least one of the current waveform measurements, the current interpretative statements, and the serial comparison statements, and to present the unread group of current ECG records in a prioritized order such that the unread group of current ECG records are overread by a clinician in the prioritized order.

2. The system of claim 1, wherein the triage module is further executable on the processor to add a new current ECG record in the unread group to the prioritized order for clinician overreading according to the set of prioritization rules.

3. The system of claim 1, wherein the set of prioritization rules includes instructions to:
    categorize each of the current ECG records in the unread group into one of at least two clinical severity categories based on at least the current interpretive statements and the serial comparison statements and order the current ECG records within each clinical severity category from oldest to newest according to test date and time to created categorized current ECG records; and
    order the categorized ECG records according to a ranking of clinical severity categories to generate a prioritized order for clinician overreading.

4. The system of claim 3, wherein the triage module is further executable on the processor to:
    identify, based on the interpretive statement, a presence or an absence of a critical test result, wherein the critical test result is identified according to a healthcare facility's critical values policy; and
    categorize the current ECG records in the unread group into one of the at least two clinical severity categories based further on the presence or the absence of the critical test result.

5. The system of claim 4, wherein the set of prioritization rules includes instructions to categorize current ECG records in the unread group into a first clinical severity category if the current interpretive statement and/or the serial comparison statement of the respective current ECG record indicate a change from normal previous ECG data to abnormal current ECG data and the presence of the critical test result.

6. The system of claim 5, wherein the triage module is further executable on the processor to:
identify, based on the interpretive statement, a presence or an absence of a high severity result, wherein the high severity result indicates any of one of a predefined list of arrhythmias or heart attack indicators; and
categorize the current ECG records in the unread group into one of the at least two clinical severity categories based further on the presence or the absence of the high severity result.

7. The system of claim 6, wherein the set of prioritization rules includes instructions to: categorize current ECG records in the unread group into a second clinical severity category if the current interpretive statement and/or the serial comparison statement of the respective current ECG record indicate the change from normal previous ECG data to abnormal current ECG data, the absence of the critical test result, and the presence of the high severity result; and
generate the prioritized order for clinician overreading with the first clinical severity category ranked before the second clinical severity category.

8. The system of claim 7, wherein the set of prioritization rules includes instructions to:
categorize current ECG records in the unread group into a third clinical severity category if the current interpretive statement and the serial comparison statement of the respective current ECG record indicate the change from normal previous ECG data to abnormal current ECG data, the absence of the critical test result, and the absence of the high severity result; and
generate the prioritized order for clinician overreading with the first clinical severity category and the second clinical severity category ranked before the third clinical severity category.

9. The system of claim 8, wherein the set of prioritization rules includes instructions to:
categorize current ECG records in the unread group into a fourth clinical severity category if the current interpretive statement and/or the serial comparison statement of the respective current ECG record indicate an abnormal previous ECG data and abnormal current ECG data, and the presence of a critical test result; and
generate the prioritized order for clinician overreading with the first clinical severity category and the second clinical severity category ranked before the third clinical severity category and the fourth clinical severity category.

10. The system of claim 9, wherein the set of prioritization rules includes instructions to rank the fourth clinical severity category before the third clinical severity category.

11. The system of claim 9, wherein the set of prioritization rules includes instructions to:
categorize current ECG records in the unread group into a fifth clinical severity category if the current interpretive statement and/or the serial comparison statement of the respective current ECG record indicate an abnormal previous ECG data and abnormal current ECG data, and the absence of a critical test result; and
generate the prioritized order for clinician overreading with the first clinical severity category, the second clinical severity category, the third clinical severity category, and the fourth clinical severity category ranked before the fifth clinical severity category.

12. The system of claim 5, wherein the set of prioritization rules includes instructions to:
categorize current ECG records in the unread group into a third clinical severity category if the current interpretive statement and/or the serial comparison statement of the respective current ECG record indicate the change from normal previous ECG data to abnormal current ECG data and the absence of the critical test result; and
generate the prioritized order for clinician overreading with the first clinical severity category ordered before the third clinical severity category.

13. A method for processing ECG records from multiple patients for clinician overreading, the method comprising:
identifying an unread group of current ECG records from multiple patients awaiting clinician overreading, wherein each current ECG record in the unread group includes at least:
a current ECG data recorded from a patient,
a current waveform measurement of the current ECG data,
a current interpretive statement of the current ECG data, and
a serial comparison statement comparing at least one of the current waveform measurements to previous waveform measurements of a previous ECG data from the patient and the current interpretive statements to previous interpretive statements of the previous ECG data from the patient;
applying, with a processor, a set of prioritization rules to prioritize the current ECG records in the unread group into a prioritized order for clinician overreading based on at least one of the current waveform measurements, the current interpretative statements, and the serial comparison statements; and
presenting the current ECG records in the prioritized order for clinician overreading such that the unread group of current ECG records are overread by a clinician in the prioritized order.

14. The method of claim 13, further comprising adding a new current ECG record to the unread group according to the set of prioritization rules so as to maintain the unread group in the prioritized order.

15. The method of claim 13, wherein executing the set of prioritization rules includes: categorizing each of the current ECG records in the unread group into one of at least two clinical severity categories based on at least the current interpretive statements and/or the serial comparison statements and ordering the current ECG records within each clinical severity category from oldest to newest according to test date and time to create categorized ECG records; and
ordering the categorized ECG records according to a ranking of clinical severity categories to generate a prioritized order for clinician overreading.

16. The method of claim 15, further comprising identifying, based on the interpretive statement, a presence or an absence of a critical test result, wherein the critical test result is identified according to a healthcare facility's critical values policy; and
dividing the current ECG records in the unread group into one of the at least two clinical severity categories based further on the presence or the absence of the critical test result.

17. The method of claim 16, wherein executing the set of prioritization rules includes categorizing current ECG records in the unread group into a first clinical severity category if the current interpretive statement and/or the serial comparison statement of the respective current ECG record indicate a change from normal previous ECG data to abnormal current ECG data and the presence of the critical test result.

18. The method of claim 17, further comprising identifying, based on the interpretive statement, a presence or an absence of a high severity result, wherein the high severity result indicates any of one of a predefined list of arrhythmias or heart attack indicators; and
    dividing the current ECG records in the unread group into one of the at least two clinical severity categories based further on the presence or the absence of the high severity result.

19. The method of claim 18, wherein executing the set of prioritization rules includes categorizing current ECG records in the unread group into a second clinical severity category if the current interpretive statement and the serial comparison statement of the respective current ECG record indicate the change from normal previous ECG data to abnormal current ECG data, the absence of the critical test result, and the presence of the high severity result; and
    generating the prioritized order for clinician overreading with the first clinical severity category ranked before the second clinical severity category.

\* \* \* \* \*